United States Patent [19]

Schefczik et al.

[11] 3,946,017
[45] Mar. 23, 1976

[54] LACTONES OF THE BENZAXANTHERE SERIES AND DYE-FORMING COMPONENTS FOR USE IN DUPLICATION PROCESSES

[75] Inventors: Ernst Schefczik, Ludwigshafen; Hellmut Kast, Bobenheim-Roxheim, both of Germany

[73] Assignee: Badische Anilin- & Soda-Fabrik Aktiengesellschaft, Ludwigshafen (Rhine), Germany

[22] Filed: Jan. 24, 1974

[21] Appl. No.: 436,043

[30] Foreign Application Priority Data

Jan. 25, 1973 Germany............................ 2303483

[52] U.S. Cl...... 260/287 C; 260/281 G; 260/289 K; 260/307 A; 260/326 A; 260/326 R; 260/326 N; 260/517; 8/1 D; 8/7; 8/2.5 R; 8/79; 427/144
[51] Int. Cl.²....................................... C07D 491/22

[58] Field of Search..................... 260/287 R, 287 C

[56] References Cited
UNITED STATES PATENTS
3,822,270   7/1974   Reynolds........................ 260/287 R OTHER PUBLICATIONS
Gove et al., "Chemistry of Natural and Synthetic Colouring Matters," 1962 p. 22cf.

*Primary Examiner*—Donald G. Daus
*Assistant Examiner*—David E. Wheeler
*Attorney, Agent, or Firm*—Johnston, Keil, Thompson & Shurtleff

[57] ABSTRACT

Lactones of the benzazaxanthene series based on 4-dialkylaminobenzoic acid compounds and homophthalic acid imides. The new lactones are eminently suitable as dye-forming components in the red range for pressure-sensitive recording material.

6 Claims, No Drawings

LACTONES OF THE BENZAXANTHENE SERIES AND DYE-FORMING COMPONENTS FOR USE IN DUPLICATION PROCESSES

This invention relates to new lactones of the benzazaxanthene series having the formula I

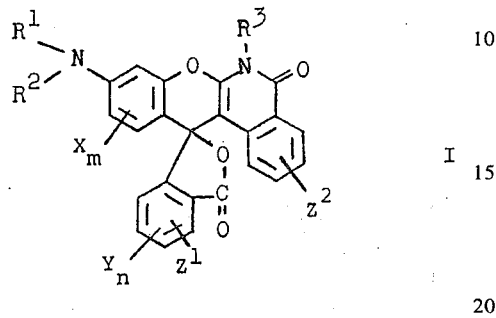

I where
R$^1$ and R$^2$ denote hydrogen, alkyl, cyanoalkyl and hydroxyalkyl with 1 to 6 carbon atoms in the alkyl radical, alkoxyalkyl of 2 to 12 carbon atoms, carbalkoxyalkyl of 4 to 11 carbon atoms, or phenylalkyl of 7 to 12 carbon atoms, and R$^1$ and R$^2$ may together form a ring, R$^3$ denotes hydrogen or an unsubstituted or substituted aliphatic or aromatic radical, X and Y denote hydrogen, hydroxy, chlorine, bromine or alkyl of 1 to 3 carbon atoms, Z$^1$ denotes hydrogen, chlorine, bromine, nitro, alkyl, hydroxyalkyl or haloalkyl with 1 to 3 carbon atoms in the alkyl radical, Z$^2$ denotes hydrogen, chlorine, bromine, alkyl of 1 to 4 carbon atoms, or phenyl, and m and n denote the integers 1, 2 or 3.

The lactones of the formula I are colorless compounds. Used as such or dissolved in non-polar or weakly polar solvents such as hydrocarbons, chlorohydrocarbons, esters or ketones, they react with acid substances, with cleavage of the lactone ring, to form the corresponding deeply colored dye salts. Since this reaction is caused even by substances such as china clay, zeolites, bentonites, silica and phenolic condensation products, which are suitable for coating, or incorporation in, paper, the lactones of this invention are outstandingly suitable as dye-forming components for pressure-sensitive recording materials, especially for the production of duplication papers. Most of the shades obtained are in the red range. The dye-forming reaction, on contacting the lactones with acidic substances, takes place instantaneously and completely, and the shade produced is distinguished by particularly high intensity and brilliance.

Apart from hydrogen, preferred examples of suitable radicals for the compounds of formula I are as follows:

R$^1$ and R$^2$: methyl, ethyl, propyl, butyl, β-hydroxyethyl, β-hydroxypropyl, β-carbomethoxyethyl, β-carboethoxyethyl;

R$^3$: alkyl of 1 to 20 carbon atoms such as methyl, ethyl, n-propyl, i-propyl, n-butyl, i-butyl, s-butyl, tert-butyl, n-pentyl, 1,4-dimethylpentyl, n-hexyl, 5-methylhexyl, 2-ethylhexyl, n-decyl, 2-methylnonyl, n-dodecyl, n-tridecyl, stearyl, cyano- and hydroxyalkyl of 1 to 6 carbon atoms such as 2-cyanoethyl, ω-cyanopentyl, ω-cyanohexyl, 2-hydroxyethyl, 2-hydroxypropyl, 2-hydroxypropyl, 1-methyl-2-hydroxypropyl, 2-methyl-2-hydroxypentyl, ω-hydroxyhexyl, alkoxyalkyl of 2 to 12 carbon atoms such as 2-methoxyethyl, 2-ethoxyethyl, 2-isopropyloxyethyl, 3-methoxypropyl, 3-ethoxypropyl, 3-isopropyloxypropyl, 3-(2-ethylhexoxy)-propyl, mono- and dialkylaminoalkyl of 2 to 10 carbon atoms such as 2-dimethylaminoethyl, 2-isopropylaminoethyl, 3-dimethylaminopropyl, 3-diethylaminopropyl, 3-isopropylaminopropyl, 1-diethylaminopentyl(2), Acyloxyalkyl of 3 to 18 carbon atoms such as 2-acetoxyethyl, 2-propionyloxyethyl, 3-acetoxypropyl, 3-propionyloxypropyl, carbalkoxyalkyl of 2 to 11 carbon atoms such as methoxycarbonylethyl, ethoxycarbonylethyl, acylaminoalkyl of 3 to 9 carbon atoms such as dimethylaminocarbonylmethyl, dimethylaminocarbonylethyl, diethylaminocarbonylethyl, butylaminocarbonylethyl, 2-ethylhexylaminocarbonylethyl, acetylaminoethyl, propionylaminoethyl, acetylaminopropyl, acetylaminobutyl, propionylaminobutyl, benzoylaminoalkyl of 9 to 13 carbon atoms such as benzoylaminoethyl, benzoylaminobutyl, phenylalkyl of 7 to 12 carbon atoms such as 2-phenylethyl, 2-methyl-2-phenylethyl, cycloalkyl of 5 to 7 carbon atoms such as cyclopentyl, cyclohexyl, phenyl, naphthyl, phenyl or naphthyl substituted by chlorine, bromine, hydroxy, trifluoromethyl, alkyl and alkoxy having 1 to 4 carbon atoms in the alkyl radical such as 2-phenylethyl, 2-methyl-2-phenylethyl, cyclopentyl, cyclohexyl, 2-methylphenyl, 3-methylphenyl, 4-methylphenyl, 2,4-dimethylphenyl, 2-ethylphenyl, 4-ethylphenyl, 2-chlorophenyl, 3-chlorophenyl, 4-chlorophenyl, 2-bromophenyl, 4-bromophenyl, 2-trifluoromethylphenyl, 3-trifluoromethylphenyl, 2-methyl-4-chlorophenyl, 2-methoxyphenyl, 3-methoxyphenyl, 4-methoxyphenyl, 4-ethoxyphenyl, 2,4-dimethoxyphenyl, 3-chloro-4,6-dimethoxyphenyl, 4-hydroxyphenyl, tetrahydronaphthyl-(1), 2-methoxynaphthyl-(1), 2-ethoxynaphthyl-(1), polyglycol radicals of 4 to 8 carbon atoms which may be etherified by alkyl radicals of 1 to 4 carbon atoms or esterified by acyl radicals of 2 or 3 carbon atoms, such as β-(β'-hydroxyethoxy)-ethyl and β-(β'-acetyloxyethoxy)-ethyl, and the radicals of the formulae

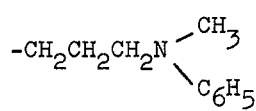 , 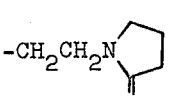 , 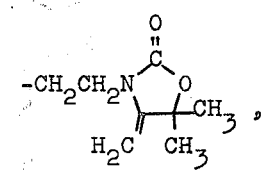 ,

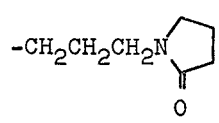 , 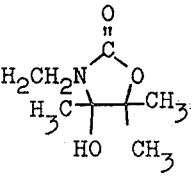 , 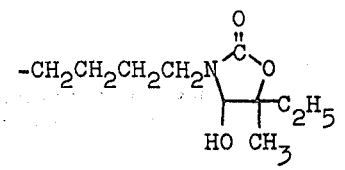 ,

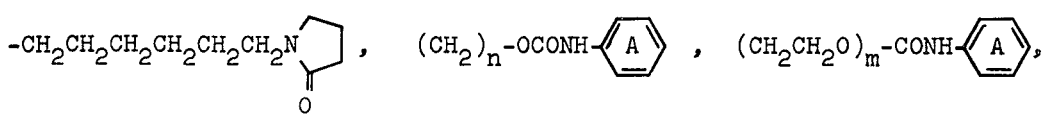

X: methyl, ethyl, propyl, chlorine,
Y: chlorine,
Z¹: methyl, ethyl, trifluoromethyl, nitro,
Z²: methyl, ethyl, chlorine, bromine, phenyl.

The lactones of formula I in which R¹ and R² denote methyl and/or ethyl and X, Y, Z¹ and Z² denote hydrogen, and among them the compounds of the formulae

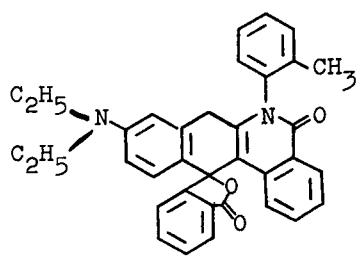

and

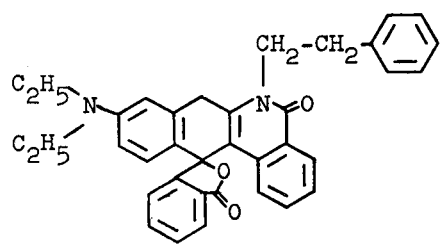

are of particular industrial importance as dye-forming components.

The benzazaxanthene lactones of formula I are prepared in a conventional manner by condensation of benzoylbenzoic acid of formula

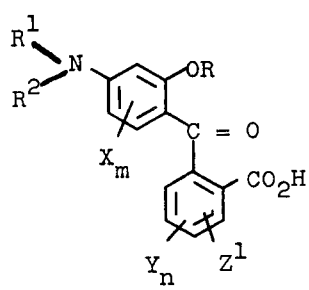

in which R denotes hydrogen or a lower alkyl or acyl radical with a homophthalimide of formula III

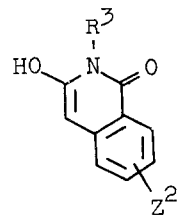

The condensation is advantageously carried out in the presence of water-eliminating agents such as sulfuric acid, polyphosphoric acid, acetic anhydride or zinc chloride at elevated temperature, e.g. at from 60° to 160°C, optionally in the presence of a high-boiling solvent such as trichlorobenzene. As a rule the reaction is over after 2 to 6 hours. For the purpose of processing, the reaction product may be introduced, after it has been allowed to cool, into a dilute aqueous alkali or ammonium hydroxide solution, from which the insoluble reaction product can be separated; the product may then be purified, e.g. by reprecipitation or recrystallization. In many cases the reaction product crystallizes out from the condensation mixture; it may then be separated and purified by reprecipitation or recrystallization.

The lactones obtained may be used as dye-forming components for pressure-sensitive recording materials, e.g. in duplicating methods. They may for example be made into a paste, the latter is applied to paper, and the surface is provided with a protective layer. A particularly advantageous application consists in enclosing the dye-forming component dissolved in a non-volatile or sparingly volatile solvent, e.g. chloroparaffin, trichlorodiphenyl, and alkylbenzene bearing one or more substituents, in microcapsules and applying these to paper. Under the writing pressure the microcapsules are brought into contact with an acid receptive layer with the result that the characters appear. It is also possible for the acid component and the microcapsules to be present in a single layer.

The invention is illustrated by the following Examples, in which parts and percentages are by weight.

EXAMPLE 1

A mixture of 313 parts of 2-(4'-diethylamino-2'-hydroxybenzoyl)-benzoic acid, 265 parts of N-phenylethylhomophthalimide and 1100 parts of acetic anhydride is refluxed for 5 hours. The reaction mixture is allowed to cool, poured onto ice and neutralized with caustic soda solution. The precipitate is filtered off, washed with water and dried. The crude product is recrystallized from toluene; 453 parts of the compound of the formula

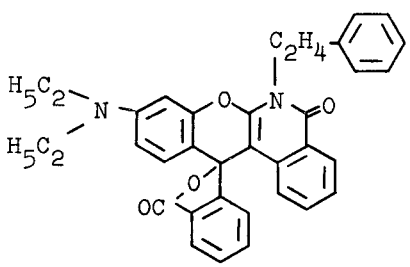

is obtained (melting point 200° to 202°C).

A solution of this compound in dodecylbenzene is enclosed in microcapsules, which are applied to paper. During writing in the presence of an acid receptive layer the microcapsules are destroyed and their contents come into contact with the acid receptive layer; the characters thus obtained are bluish red.

The following starting compounds are treated as described in Example 1. There are obtained dye-forming components which give the shades indicated in the Table when contacted with acid substances during writing.

is obtained (melting point 218° to 220°C).

EXAMPLE 21

A mixture of 313 parts of 2-(4'-diethylamino-2'-hydroxybenzoyl)-benzoic acid, 175 parts of N-methyl-homophthalimide and 1100 parts of acetic anhydride is heated under reflux for 5 hours. After cooling, the precipitate is filtered off and washed, first with acetic acid and then with methanol. After drying at 60°C, 390 parts of the compound having the formula

| Example | Benzoylbenzoic acid component | Homophthalimide component | Shade | Melting point of dye-forming compound (°C) |
|---|---|---|---|---|
| 2 | 2-(4'-diethylamino)-2'-hydroxybenzoyl-benzoic acid | N-ethylhomo-phthalimide | bluish red | 284 to 286 |
| 3 | " | N-3-(2'-ethyl-hexoxy)-propyl-homophthalimide | " | 162 to 165 |
| 4 | " | N-3-(2'-phenoxy-ethoxy)-propyl-homophthalimide | " | 154 to 157 |
| 5 | " | N-2-ethylhexoxy-homophthalimide | " | 198 to 200 |
| 6 | " | N-3-ethoxypropyl-homophthalimide | " | 166 to 169 |
| 7 | " | N-butylhomo-phthalimide | " | not measured |
| 8 | " | N-hexylhomo-phthalimide | " | not measured |
| 9 | " | N-dodecylhomo-phthalimide | " | " |
| 10 | " | N-3-diethylamino-propylhomophthal-imide | " | " |
| 11 | " | N-cyclohexyl-homophthalimide | " | " |
| 12 | " | N-2-methyl-2-phenylethyl-homophthalimide | " | " |
| 13 | " | N-o-tolylhomo-phthalimide | red | 221 to 224 |
| 14 | " | N-p-tolylhomo-phthalimide | red | 270 to 273 |
| 15 | 2-(4'-dimethylamino)-2'-hydroxybenzoyl-benzoic acid | N-phenylethyl-homophthalimide | red | 276 to 278 |
| 16 | " | N-butylhomo-phthalimide | red | not measured |
| 17 | " | N-hexylhomo-phthalimide | red | not measured |
| 18 | 2-(4'-dimethylamino)-2'-hydroxybenzoyl-benzoic acid | N-dodecylhomo-phthalimide | red | not measured |
| 19 | " | N-stearylhomo-phthalimide | " | not measured |

EXAMPLE 20

313 Parts of 2-(4'-diethylamine-2'-hydroxybenzoyl)-benzoic acid and 217 parts of N-butylhomophthalimide are heated in 1500 parts of concentrated sulfuric acid at 80°C for 5 hours. After cooling, the reaction mixture is poured onto ice and neutralized with caustic soda solution and the precipitate is filtered off. After recrystallization from ethanol 412 parts of the compound having the formula

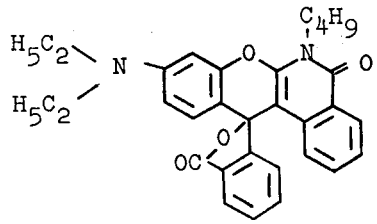

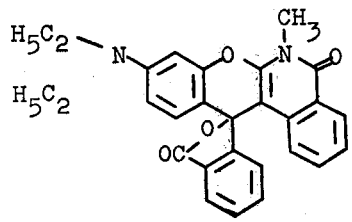

is obtained (melting point 301° to 303°C).

We claim:
1. A lactone of the benzazaxanthene series of the formula

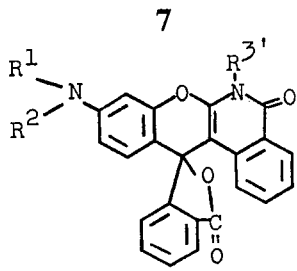

wherein
R¹ and R² denote methyl or ethyl, and
R³ denotes alkyl of from 1 to 20 carbon atoms, alkoxyalkyl of from 2 to 12 carbon atoms, 3-diethylaminopropyl, 2-phenylethyl, 2-methyl-2-phenylethyl, 3-(2'-phenoxyethoxy)-propyl, o-tolyl, p-tolyl or cyclohexyl.

2. A lactone of the formula as claimed in claim 1 wherein R³ denotes alkyl of from 1 to 20 carbon atoms.

3. A lactone of the formula as claimed in claim 1 wherein R³ denotes alkoxyalkyl of from 2 to 12 carbon atoms.

4. The compound of the formula

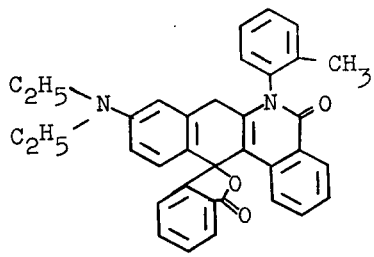

5. The compound of the formula

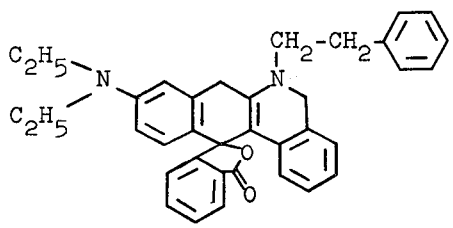

6. A lactone of the formula

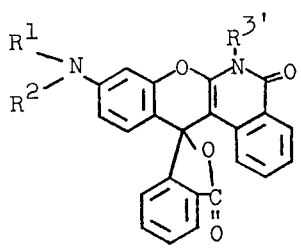

wherein
R¹ and R² denote methyl or ethyl,
R³' denotes methyl, ethyl, butyl, hexyl, dodecyl, stearyl, 3-(2-ethylhexoxy)-propyl, 2-hexoxyethyl, 3-ethoxypropyl, 3-(2'-phenoxyethoxy)-propyl, 3-diethylaminopropyl, 2-phenylethyl, 2-methyl-2-phenylethyl, o-tolyl or p-tolyl.

* * * * *